(12) United States Patent
Galavotti

(10) Patent No.: US 7,371,567 B2
(45) Date of Patent: May 13, 2008

(54) BIOREACTOR, PARTICULARLY FOR BIOARTIFICIAL ORGANS

(75) Inventor: Daniele Galavotti, Mirandola (IT)

(73) Assignee: Rand S.R.L., Medolla (IT)

( * ) Notice: Subject to any disclaimer, the term of this patent is extended or adjusted under 35 U.S.C. 154(b) by 732 days.

(21) Appl. No.: 10/802,726

(22) Filed: Mar. 18, 2004

(65) Prior Publication Data
US 2005/0142530 A1 Jun. 30, 2005

(30) Foreign Application Priority Data
Mar. 21, 2003 (IT) .......................... MO2003A0081

(51) Int. Cl.
*C12M 3/06* (2006.01)
(52) U.S. Cl. ............... 435/297.4; 435/299.1; 210/321.87
(58) Field of Classification Search ............ 435/297.4, 435/299.1; 210/321.87
See application file for complete search history.

(56) References Cited

U.S. PATENT DOCUMENTS

| 4,720,462 | A |   | 1/1988 | Rosenson |
| 5,516,691 | A | * | 5/1996 | Gerlach .................... 435/297.1 |
| 6,372,495 | B1 |   | 4/2002 | Flendring |
| 2002/0168758 | A1 |   | 11/2002 | Martinez |

FOREIGN PATENT DOCUMENTS

| DE | 41 23 125 A | 1/1993 |
| EP | 0 356 785 A | 3/1990 |
| EP | 0 419 234 A | 3/1991 |
| EP | 0 909 811 A | 4/1999 |
| WO | 02/18535 A | 3/2002 |

\* cited by examiner

*Primary Examiner*—William H. Beisner
(74) *Attorney, Agent, or Firm*—Collard & Roe, P.C.

(57) ABSTRACT

A bioreactor for bioartificial organs, comprising a closed and substantially tubular body inside which there is a containment cavity; an animal and/or human cell culture and support structure, accommodated in the cavity and suitable to be crossed by a fluid to be processed; a port for the inflow of the fluid to be processed, which is formed in the body upstream of the structure; a port for the outflow of the processed fluid, which is formed in the body downstream of the structure; a first chamber for collecting the fluid to be processed, which is formed in the cavity upstream of the structure and is connected to the outside of the body by means of the inflow port; a second chamber for collecting the processed fluid, which is formed in the cavity downstream of the structure and is connected to the outside of the body by means of the outflow port; a first bundle of hollow capillary fibers for the inflow of the fluid to be processed, which is accommodated in the cavity and is interposed between the first collection chamber and the structure, and a second bundle of hollow capillary fibers for the outflow of the processed fluid, which is accommodated in the cavity and is interposed between the structure and the second collection chamber, the flow of the fluid being substantially parallel to the longitudinal axis of the bioreactor.

29 Claims, 3 Drawing Sheets

BIOREACTOR, PARTICULARLY FOR BIOARTIFICIAL ORGANS

The present invention relates to a bioreactor, particularly for bioartificial organs.

BACKGROUND OF THE INVENTION

Bioreactors used in the biological, microbiological and medical field, for example for the perfusion of cultures of animal or human cells or for the creation of bioartificial organs, where the expression "bioartificial organ" is used to designate extracorporeal devices capable of supporting or temporarily compensating for insufficient functions of organs of a human being, have long been known.

Bioreactors used to create bioartificial organs can host cultures of animal or human cells capable of reproducing the specific functions of the organ to be supported.

Merely by way of example, bioreactors are used to create bioartificial livers, which are extracorporeal devices substantially constituted by a filtration unit, which separates the fluid to be processed, plasma or ultrafiltrate, from the corpuscular components of blood drawn from a patient; by a bioreactor, which contains a culture of metabolically active hepatocytes and is crossed by the fluid to be processed; and by a unit for recombining the processed fluid in output from the bioreactor with the corpuscular components of the blood, which is then reinjected into the patient.

The bioreactor must allow contact between the fluid to be processed and the hepatocytes, so that an exchange suitable to rebalance the concentration of the components of the fluid and of the gases dissolved therein occurs, and so that at the same time the passage of hepatocytes or of fragments thereof in said fluid is prevented, in order to avoid patient immunization phenomena.

The first bioreactors used specifically for bioartificial livers were built by using dialysis machines as their model and by using the basic principles of dialysis processes.

There has been a transition from the early flat-membrane bioreactors to the more recent bioreactors with bundles of hollow capillary fibers, on the outside or inside of which the cell cultures are accommodated.

The use of hollow capillary fibers has allowed to improve diffusion and exchange processes between the fluid to be processed and the cell cultures and to provide the oxygen input required for the metabolism of these cultures.

However, these known bioreactors have had some drawbacks, including the fact that the exchange between the cell culture that they host and the fluid to be processed that passes through them occurs unevenly, inconstantly and partially on the useful exchange surface, with a consequent limited utilization of their actual exchange capacity and a reduction of their efficiency.

This is due both to the low pressure at which it is necessary to introduce the fluid to be processed, in order to avoid subjecting the cells of the culture to stresses that would compromise their vitality, and to the shape and configuration of the supporting structure of the cell cultures, which cause a concentration of the exchange at the region where the fluid enters the bioreactor instead of distributing it over the entire useful surface.

Another drawback of known bioreactors is that the useful volume for the cell culture is greatly reduced with respect to their total volume, the former being on the order of one third of the latter; this, combined with the need to have a sufficient cell concentration capable of replacing the functions of the organ to be supported, entails an increase in the overall dimensions of bioreactors.

In order to obviate these drawbacks, bioreactors with hollow capillary fibers are known which are essentially constituted by a substantially tubular container which internally accommodates a cell culture and support structure and is provided, at one end, with a port for the inflow of the fluid to be processed, which is arranged upstream of the structure, and at the opposite end with a port for the outflow of the processed fluid, which is arranged downstream of the structure.

Upstream of the support and culture structure there is a first chamber for collecting the fluid to be processed, which is connected to the outside of the container by means of the inflow port; downstream of the support and culture structure there is a second chamber for collecting the processed fluid, which is connected to the outside of the container by means of the outflow port.

The support and culture structure is constituted by a multilayer panel, which is wound in a spiral around a coupling stem that is substantially coaxial to the container, is internally hollow and has a blind end and another open end that is connected to the outside of said container.

The panel has an edge that is rigidly coupled, by interlocking and/or gluing, to a longitudinal slit formed in the stem, and the opposite edge that is in contact with the inside wall of the container; the opposite ends of the spiral are embedded in a respective containment ring.

The panel is constituted by at least six superimposed flat layers: a first layer, constituted by an order of capillary hollow fibers for the outflow of the processed fluid, which are parallel to the axis of the container and are bent in a U-shape so that their free ends lead into the second collection chamber; a second layer, which is constituted by a permeable and filtering cell support medium; a third layer, which is constituted by a lattice for distribution of the cells to be seeded; a fourth layer, which is identical to the second layer; a fifth layer, which is constituted by an order of capillary hollow fibers for the inflow of the fluid to be processed, which are parallel to the axis of the container and are bent in a U-shape in the opposite direction with respect to the fibers of the first layer, so that their free ends lead into the first collection chamber; and finally, a sixth layer, which is constituted by an impermeable sheet that separates the capillary fibers of the first and fifth layer when the panel is wound in a spiral.

The cells to be seeded in the culture and support structure are inoculated, through the open end of the stem, into the cavity of said stem; the inoculated cells diffuse throughout the structure through the edge of the panel that is fixed to the stem.

Once seeding of the cells has ended, the bioreactor can be used as a bioartificial organ: the fluid to be processed is introduced through the inflow port into the first collection chamber and from there penetrates into the inflow fibers; after saturating them, it passes through their walls, and by following a substantially radial flow it reaches the layer that supports the cells with which the exchange of solutes occurs.

The fluid thus processed, again following a flow that is substantially radial with respect to the axis of the container, reaches the outflow fibers, and penetrates inside them through their walls in order to flow out into the second collection chamber and be evacuated through the outflow port.

These last known bioreactors, while having allowed to overcome the drawbacks noted earlier by allowing to provide a uniform exchange over the entire useful surface and to better utilize the available volume, nonetheless have drawbacks, including the fact that they have a very complex structure, require long, laborious and accurate assembly operations, and require the use of various kinds of material, with a consequent increase in production costs and times.

It is noted, for example, that precise operations for interlocking and bonding the edge of the panel to the central stem with adhesive are required.

Moreover, it is noted that the multilayer panel has a very complex configuration, which requires the superimposition of a plurality of different layers, including an impermeable one that is suitable to separate the hollow inflow fibers from the outflow fibers, so as to avoid any mixing of the fluid to be processed and the already-processed fluid.

SUMMARY OF THE INVENTION

The aim of the present invention is to eliminate the above-mentioned drawbacks of known bioreactors, by providing a bioreactor, particularly for bioartificial organs, that is structurally and constructively simpler, allows to limit and facilitate assembly operations, and allows to reduce the use of different types of material and to contain production times and costs.

Within this aim, an object of the present invention is to provide a bioreactor that has a simple structure, is relatively easy to provide in practice, safe in use, effective in operation, and has a relatively low cost.

This aim and these and other objects that will become better apparent hereinafter are achieved by the present bioreactor, particularly for bioartificial organs, which comprises a closed and substantially tubular body inside which there is a containment cavity; an animal and/or human cell culture and support structure, accommodated in said cavity and suitable to be crossed by a fluid to be processed; a port for the inflow of said fluid to be processed, which is formed in said body upstream of said structure; a port for the outflow of the processed fluid, which is formed in said body downstream of said structure; a first chamber for collecting the fluid to be processed, which is formed in said cavity upstream of said structure and is connected to the outside of said body by means of said inflow port; and a second chamber for collecting the processed fluid, which is formed in said cavity downstream of said structure and is connected to the outside of said body by means of said outflow port; characterized in that it comprises a first bundle of hollow capillary fibers for the inflow of said fluid to be processed, which is accommodated in said cavity and interposed between said first collection chamber and said structure, and a second bundle of hollow capillary fibers for the outflow of said processed fluid, which is accommodated in said cavity and is interposed between said structure and said second collection chamber.

BRIEF DESCRIPTION OF THE DRAWINGS

Further characteristics and advantages of the present invention will become better apparent from the following detailed description of a preferred but not exclusive embodiment of a bioreactor, particularly for bioartificial organs, illustrated by way of non-limiting example in the accompanying drawings, wherein.

DESCRIPTION OF THE PREFERRED EMBODIMENTS

Figure 1:
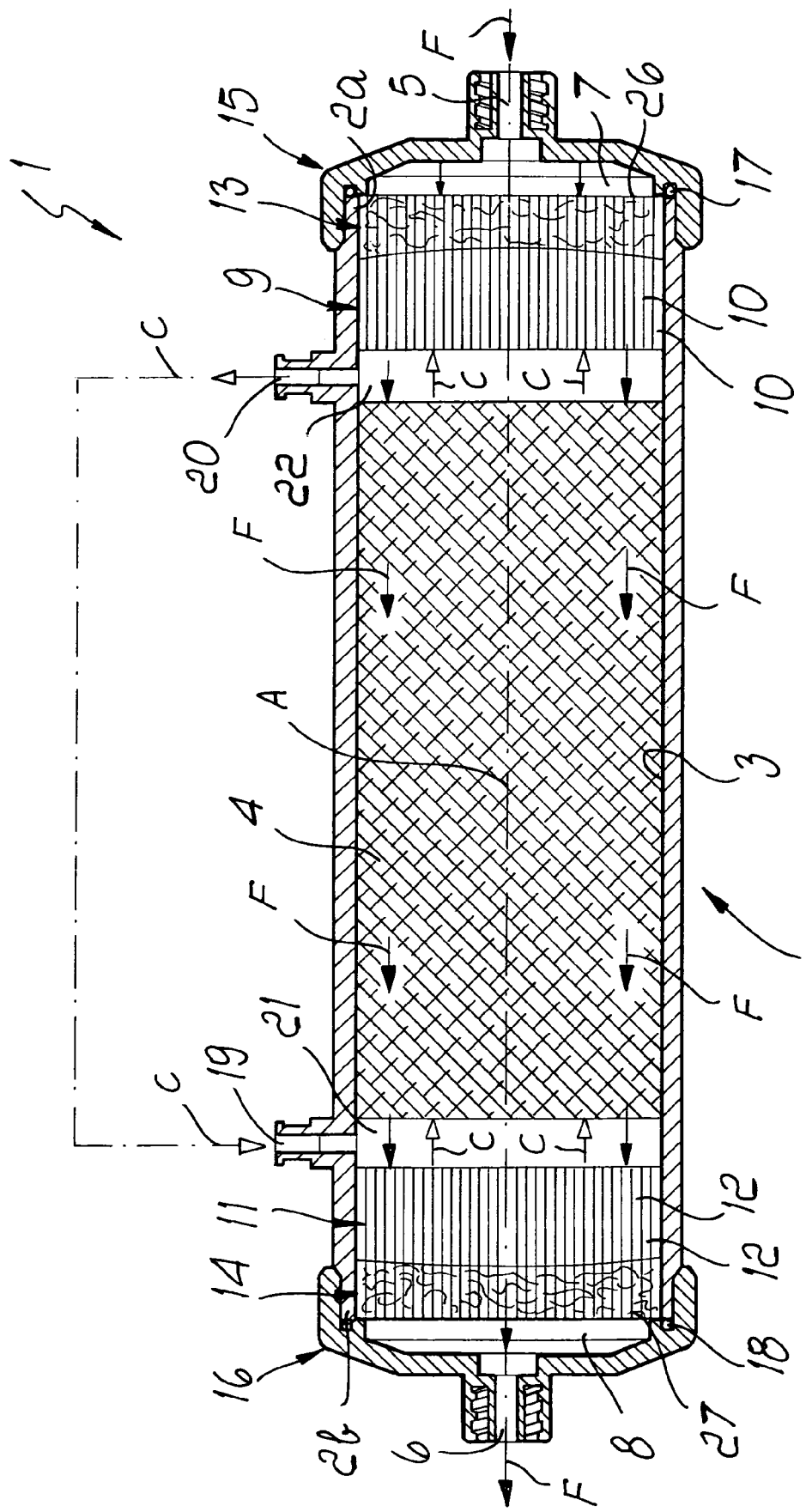
FIG. 1 is a schematic sectional view, taken along a longitudinal plane, of a bioreactor, particularly for bioartificial organs, according to the invention.
Figure 2:
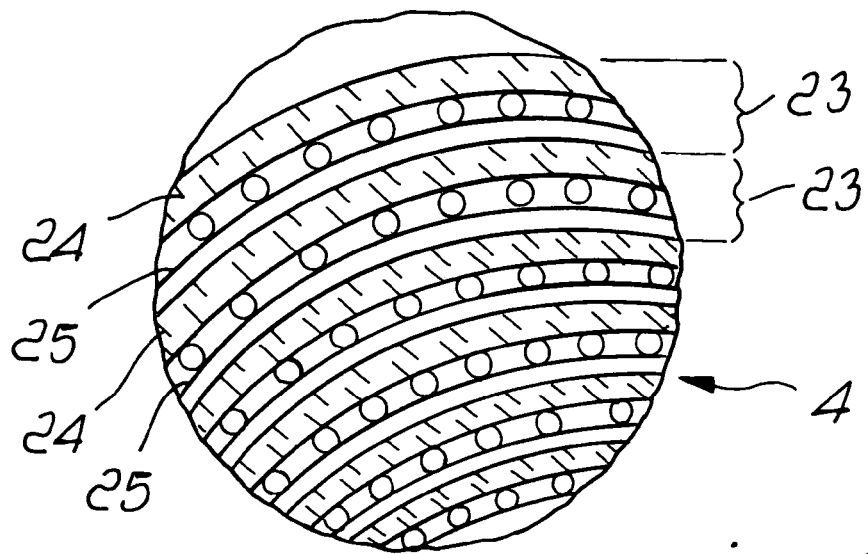
FIG. 2 is an enlarged-scale schematic sectional view, taken along a transverse plane, of a portion of the cell support and culture structure of the bioreactor according to the invention.

With reference to the figures, the reference numeral 1 generally designates a bioreactor, particularly for bioartificial organs.

The bioreactor 1 comprises a substantially tubular closed body 2, inside which there is a containment cavity 3, and an animal and/or human cell culture and support structure 4, which is accommodated in the cavity 3 and is suitable to be crossed by a fluid to be processed, such as for example plasma or ultrafiltrate.

The body 2 is provided with a port 5 for the inflow of the fluid to be processed, which is formed upstream of the structure 4, and with a port 6 for the outflow of the processed fluid, which is formed downstream of the structure 4.

Inside the cavity 3 and upstream of the structure 4 there is a first chamber 7 for collecting the fluid to be processed, which is connected to the outside of the body 2 by means of the inflow port 5; also inside the cavity 3, but downstream of the structure 4, there is a second chamber 8 for collecting the processed fluid, which is connected to the outside of the body 2 by means of the outflow port 6.

The bioreactor 1 further comprises a first bundle 9 of hollow capillary fibers 10 for the inflow of the fluid to be processed, which is accommodated in the cavity 3 and is interposed between the first chamber 7 and the structure 4, and a second bundle 11 of hollow capillary fibers 12 for the outflow of the processed fluid, which is accommodated in the cavity 3 and is interposed between the structure 4 and the second chamber 8.

First anchoring means 13 and second anchoring means 14 respectively fix the first bundle 9 and the second bundle 11 with respect to the body 2.

The body 2 comprises two opposite ends 2a and 2b, respectively upstream and downstream of the structure 4, which are closed hermetically by respective covers 15 and 16 with corresponding interposed gaskets 17 and 18.

The inflow port 5 is formed in the cover 15 and the outflow port 6 is formed in the cover 16; the two ports are substantially coaxial to the longitudinal axis of the body 2, the corresponding outline of which has been designated by the reference letter A.

The first chamber 7 remains defined between the cover 15 and the first anchoring means 13; the second chamber 8 is formed between the cover 16 and the second anchoring means 14.

Moreover, the bioreactor 1 is provided with an inlet 19 for inoculating the cells that will be cultured and supported by the structure 4 and with an outlet 20 for evacuating the inoculated cells that have not adhered to the structure 4; the inoculation inlet 19 and the evacuation outlet 20 are formed in the body 2 between the first bundle 9 and the second bundle 11.

In particular, the inoculation inlet 19 is formed between the second bundle 11 and the structure 4, while the evacuation outlet 20 is formed between the structure 4 and the first bundle 9.

A chamber 21 for the inflow of the inoculated cells is formed in the cavity 3, between the second bundle 11 and the structure 4, and is connected to the outside of the body 2 by means of the inoculation inlet 19.

A chamber 22 for the outflow of the inoculated cells that have not adhered to the structure 4 is formed in the cavity 3 between the structure 4 and the first bundle 9 and is connected to the outside of the body 2 by means of the evacuation outlet 20.

Plugs for closing the inoculation inlet 19 and the evacuation outlet 20 are provided and are not shown since they are of a known type.

The structure 4 comprises a panel 23 that is wound up in a roll or spiral so that its axis is substantially parallel to the axis A of the body 2; the longitudinal edge of the panel 23 inside the roll is free and its opposite longitudinal end is also free and in contact with the inside wall of the cavity 3.

The panel 23 is wound around said inner longitudinal edge through an arc of at least 270°.

The panel 23 comprises at least two mutually superimposed and parallel plate-like layers: a first layer 24, which is constituted by a cell support matrix, and a second layer 25, which is constituted by an inoculated cell diffusion and distribution matrix.

Advantageously, the panel 23, in an embodiment that is not shown, can comprise a third layer that is identical to the first layer 24 and is superimposed and parallel with respect to the second layer 25.

The first layer 24 is of a type that is permeable with respect to the fluid to be processed and can be constituted by sheets of polymeric fabric with a crossed weave having a random or ordered arrangement, such as for example polyester or the like.

The total volume of the first layer 24 and/or of the optional third layer is comprised between 5 and 15% of the total volume available for the cells.

The second layer 25 instead has a lattice-like structure and is made for example of polyester.

The first bundle 9 comprises one or more flat superimposed orders of hollow capillary fibers 10, which are arranged substantially parallel to the axis A of the body 2 and are individually bent in a U-shape, so that their respective open ends are directed toward the first chamber 7, such fibers 10 being permeable to the fluid to be processed. The second bundle 11 comprises one or more flat superimposed orders of hollow capillary fibers 12, which are arranged substantially parallel to the axis A of the body 2 and are individually folded in a U-shape, with their respective open ends directed toward the second chamber 8, the fibers 12 being permeable to the processed fluid.

Each fiber 10 and 12, respectively of the first bundle 9 and of the second bundle 11, is constituted by a segment of a capillary tube made of microporous material, which is bent in a U-shape substantially at the centerline so as to form two straight branches 10a and 12a that are mutually substantially parallel, with open ends that lead respectively into the first chamber 7 and into the second chamber 8.

The microporous material of which the fibers 10 and 12 are constituted has pores whose average diameter is comprised between 0.10 μm and 0.50 μm and is constituted for example by polyether sulfone or the like.

Conveniently, the distribution density and the diameter of the fibers 10 and 12 are constant along the entire extension of the first bundle 9 and of the second bundle 11 respectively.

The first anchoring means 13 and the second anchoring means 14 comprise a respective shim 26 and 27 made of a sealing material, which is accommodated snugly in the cavity 3, is arranged substantially at right angles to the axis A of the body 2, and in which the branches 10a and 12a of the fibers 10 and 12 of the first bundle 9 and of the second bundle 11 respectively are embedded at least partially.

The material of which the shims 26 and 27 are made is of the polymeric type, for example based on polyurethane or the like.

Figure 4:
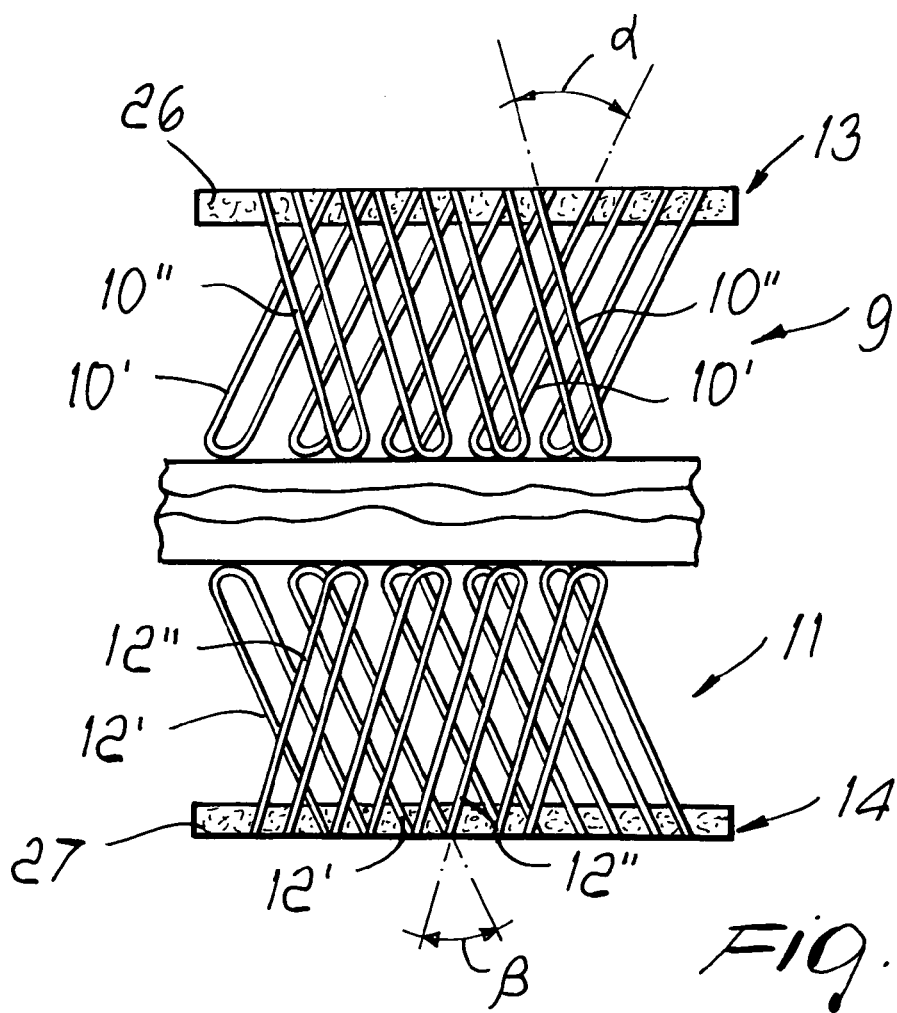
FIG. 4 is a schematic plan view of the first and second bundles of fibers of an alternative embodiment of the bioreactor according to the invention.
Figure 3:
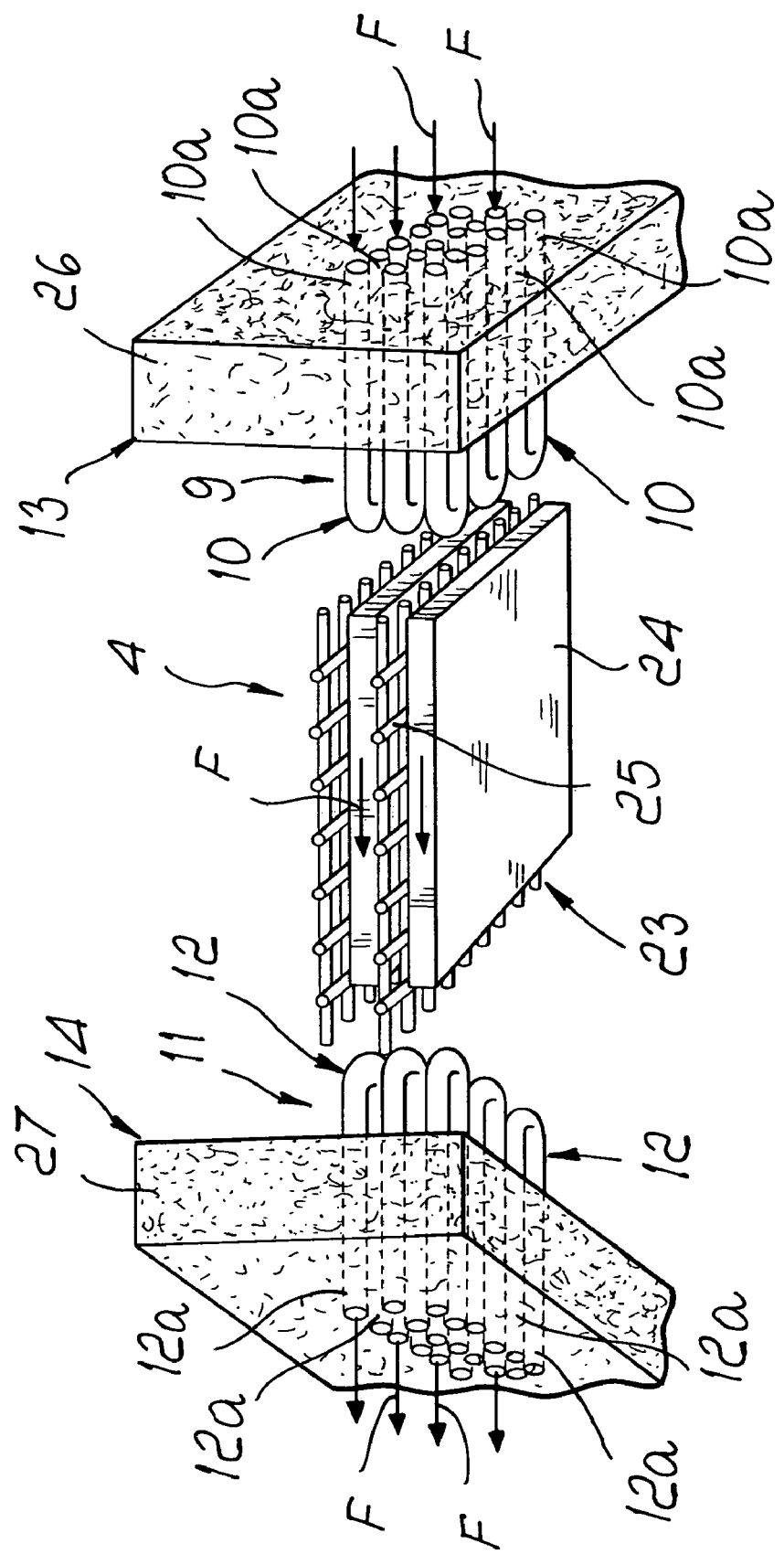
FIG. 3 is a schematic axonometric view of a portion of the cell support and culture structure and of the first and second bundles of fibers of the bioreactor according to the invention.

FIG. 4 is a view of a portion of an alternative embodiment of the bioreactor 1, in which the first bundle 9 of fibers 10 comprises at least two flat and superimposed orders of hollow capillary fibers 10' and 10", which are permeable to the fluid and are individually bent in a U-shape, so that their respective open ends are directed toward the first chamber 7; the fibers 10' of one of the two orders are arranged, with respect to the fibers 10" of the other order, at an angle α that is variable between 15° and 30°.

Likewise, the second bundle 11 of fibers 12 comprises at least two flat and superimposed orders of hollow capillary fibers 12' and 12", which are permeable to the fluid and are individually bent in a U-shape, so that their respective open ends are directed toward the second chamber 8; the fibers 12' of one of the two orders are arranged, with respect to the fibers 12" of the other order, at an angle β that is variable between 15° and 30°.

The bioreactor 1 can be used for example as a bioartificial liver; in this case, the cells that are supported and cultured on the structure 4 are hepatocytes, while the fluid processed therein is constituted by plasma or ultrafiltrate separated from the corpuscular components of the blood drawn from a patient.

The operation of the invention is as follows.

Before the bioreactor 1 can be used as a bioartificial organ, it is necessary to seed the structure 4 with the appropriate cells (hepatocytes).

The cells are injected through the inoculation inlet 19 into the inflow chamber 21, from which they flow toward the structure 4; the inoculated cells diffuse through the second layer 25 into the first layer 24 of the panel 23, to which they adhere.

The cells that do not adhere to the first layer 24 flow away toward the outflow chamber 22, from which they are removed through the evacuation outlet 20 in order to be optionally returned to circulation.

The direction of the flow of the cells inside the body 2, indicated schematically by the arrows C, has a component of diffusion from the second layer 25 to the first layer 24 that is substantially perpendicular to the axis A and a component of outflow from the inoculation inlet 19 to the evacuation outlet 20 that is substantially parallel to the axis A of the body 2.

Once the seeding of the cells has ended, the inoculation inlet 19 and the evacuation outlet 20 are closed with their respective plugs; the bioreactor 1 is thus ready to be used as a bioartificial organ.

The fluid to be processed, for example the plasma or ultrafiltrate separated from the corpuscular components of the blood drawn from a patient, is pumped through the inflow port 5 into the first chamber 7, where the open ends of the fibers 10 of the first bundle 9 lead; the pumping pressure is very low, so as to avoid compromising the integrity and therefore the vitality of the cells seeded in the structure 4.

The fluid to be processed enters the open ends of the fibers 10 and penetrates their internal opening; once it has saturated said opening, it passes the pores of the walls of the fibers 10 in order to reach the outflow chamber 22 and flow from there toward the structure 4 in a direction that is substantially parallel to the axis A of the body 2.

The fluid flows through the structure 4, always following a direction that is substantially parallel to the axis A of the body 2; inside the structure 4, it makes contact with the cells seeded therein, which perform the detoxification functions assigned to them.

The fluid thus processed pours into the inflow chamber 21, while the cells are retained inside the structure 4.

The processed fluid contained in the inflow chamber 21 passes through the pores of the walls of the fibers 12 of the second bundle 11 in order to enter their internal opening; after saturating said opening, it pours into the second chamber 8, from which it flows out, through the outflow port 6, in order to be recirculated or recombined with the corpuscular components of the blood of the patient and be reinjected into said patient.

The direction of the stream of fluid that reaches the outflow port 6 from the inflow port 5 through the structure 4 is substantially parallel to the longitudinal axis A of the body 2; the fluid crosses in succession the first chamber 7, the first bundle 9 of fibers 10, the outflow chamber 22, the structure 4, the inflow chamber 21, the second bundle 11 of fibers 12, and the second chamber 8.

The flow of the fluid is shown schematically by the arrows F; it is noted that since the bioreactor is mirror-symmetrical, the direction of the flow of the fluid may also be the opposite of the one taken as reference in the present description.

In practice it has been found that the described invention achieves the intended aim and objects.

The bioreactor according to the invention is in fact structurally and constructively simpler than known bioreactors, requires a smaller number of assembly operations, and allows to limit the use of different materials.

It is noted in fact that the bioreactor according to the invention does not have the central stem for coupling the cell culture and support structure and therefore does not require the corresponding operations for interlocking and adhesive-bonding the latter to the former.

The panel of the cell culture and support structure of the bioreactor according to the invention is constituted by the superimposition of two or three layers, instead of six, and does not require an impermeable layer to separate the processed fluid from the fluid yet to be processed.

The bioreactor according to the invention, for an equal volume, is longer (even by 200%) than known bioreactors but has a diameter that is reduced by as much as 50%, allowing to use standard commercially available containment bodies.

Finally, the bioreactor according to the invention allows, thanks to the longitudinal flow of the cells to be seeded and of the fluid to be processed, to optimize both in situ seeding of the cells and contact between the fluid and said cells.

The invention thus conceived is susceptible of numerous modifications and variations, all of which are within the scope of the appended claims.

All the details may further be replaced with other technically equivalent elements.

In practice, the materials used, as well as the shapes and dimensions, may be any according to requirements and to the state of the art without thereby abandoning the scope of the protection of the appended claims.

The disclosures in Italian Patent Application No. MO2003A000081, from which this application claims priority, are incorporated herein by reference.

What is claimed is:

1. A bioreactor, particularly for bioartificial organs, comprising
    a closed and substantially tubular body inside which there is a containment cavity;
    an animal and/or human cell culture and support structure, accommodated in said cavity and suitable to be crossed by a fluid to be processed;
    a port for the inflow of said fluid to be processed, which is formed in said body upstream of said structure;
    a port for the outflow of the processed fluid, which is formed in said body downstream of said structure;
    a first chamber for collecting the fluid to be processed, which is formed in said cavity upstream of said structure and is connected to the outside of said body by means of said inflow port;
    a second chamber for collecting the processed fluid, which is formed in said cavity downstream of said structure and is connected to the outside of said body by means of said outflow port; comprising a first bundle of hollow capillary fibers for the inflow of said fluid to be processed, which is accommodated in said cavity and interposed between said first collection chamber and said structure, and a second bundle of hollow capillary fibers for the outflow of said processed fluid, which is accommodated in said cavity and is interposed between said structure and said second collection chamber, wherein open ends of the first and second bundles of hollow fibers are aimed at the first and second collection chambers, respectively;
    at least one inlet for the inoculation of said cells, which is formed in said body between said first bundle and said second bundle of fibers;
    at least one outlet for the evacuation of the inoculated cells that have not adhered to said structure formed in said body between said first bundle and said second bundle of fibers; and
    a chamber for the inflow of the inoculated cells that is formed in said cavity, between said structure and one of said first and second bundles of fibers, and is connected to the outside of said body through said inoculation inlet.

2. The bioreactor according to claim 1, comprising first anchoring means and second anchoring means for said first bundle and said second bundle of fibers respectively.

3. The bioreactor according to claim 2, wherein said body comprises two opposite ends closed hermetically by respective covers, said inflow port being formed in one of said covers, said outflow port being formed in the other one of said covers.

4. The bioreactor according to claim 3, wherein said first collection chamber and said second collection chamber are formed respectively between said covers and said first and second anchoring means.

5. The bioreactor according to claim 2, wherein said first anchoring means and said second anchoring means comprise at least one layer of sealing material that is accommodated snugly in said cavity, is arranged substantially at right angles to the longitudinal axis of said body, and in which the fibers of said first bundle and of said second bundle respectively are embedded at least partially.

6. The bioreactor according to claim 5, wherein said sealing material is of the polymeric type based on polyurethane or the like.

7. The bioreactor according to claim 1, comprising a chamber for the outflow of the cells that have been inoculated and have not adhered, said chamber being formed in said cavity, between said structure and one of said first and second bundles of fibers, and being connected to the outside of said body through said evacuation outlet.

8. The bioreactor according to claim 7, wherein said inflow chamber and said outflow chamber are formed respectively between said second bundle of fibers and said structure and between said structure and said first bundle of fibers.

9. The bioreactor according to claim 1, comprising plugs for closing said inoculation inlet and said evacuation outlet.

10. The bioreactor according to claim 1, wherein said structure comprises a panel that is wound on itself in a roll or spiral with an axis that is substantially parallel to the longitudinal axis of said body, the longitudinal edge of said panel arranged inside said roll or spiral being free, the opposite longitudinal end being free and in contact with the inside wall of said cavity.

11. The bioreactor according to claim 10, wherein said panel is wound around said internal longitudinal edge through an arc of at least 270 degree.

12. The bioreactor according to claim 10, wherein said panel comprises at least two mutually superimposed and parallel plate-like layers, a first layer comprising a matrix for supporting said cells, a second layer comprising a matrix for diffusing and distributing the inoculated cells.

13. The bioreactor according to claim 12, wherein said panel comprises a third layer that is identical to said first layer and is superimposed on said second layer and parallel thereto.

14. The bioreactor according to claim 13, wherein said first layer and/or said third layer are permeable with respect to said fluid.

15. The bioreactor according to claim 13, wherein said first layer and/or said third layer are constituted by sheets of polymeric fabric having a crossed weave with a random or ordered arrangement.

16. The bioreactor according to claim 15, wherein said polymeric fabric of said first layer and/or of said third layer is made of polyester or the like.

17. The bioreactor according to claim 15, wherein the total volume of said first layer and/or said third layer is comprised between 5 and 15% of the total volume available for said cells.

18. The bioreactor according to claim 12, wherein said second layer has a lattice-like structure.

19. The bioreactor according to claim 1, wherein said first bundle of fibers comprises at least one flat order of hollow capillary fibers that are arranged substantially parallel to the longitudinal axis of said body and are individually bent in a U-shape, with their respective open ends directed toward said first collection chamber, said fibers being permeable to said fluid.

20. The bioreactor according to claim 1, wherein said first bundle of fibers comprises at least two flat and superimposed orders of hollow capillary fibers that are permeable to said fluid and are individually bent in a U-shape, with their respective open ends directed toward said first collection chamber, the fibers of one of said two orders being arranged at an angle, with respect to the fibers of the other order, that is variable between 15 and 30 degree.

21. The bioreactor according to claim 1, wherein said second bundle of fibers comprises at least one flat order of hollow capillary fibers that are arranged substantially parallel to the longitudinal axis of said body and are individually folded in a U-shape, their respective open ends being directed toward said second collection chamber, said fibers being permeable to said fluid.

22. The bioreactor according to claim 1, wherein said second bundle of fibers comprises at least two flat and superimposed orders of hollow capillary fibers that are permeable to said fluid and are individually bent in a U-shape, their respective open ends being directed toward said second collection chamber, the fibers of one of said two orders being arranged, with respect to the fibers of the other order, at an angle that can vary between 15 degree and 30 degree.

23. The bioreactor according to claim 1, wherein each one of said fibers of said first bundle and of said second bundle is constituted by a segment of a capillary tube made of microporous material which is bent in a U-shape substantially at the centerline so as to form two straight branches which are mutually substantially parallel and have open ends that lead respectively into said first collection chamber and into said second collection chamber.

24. The bioreactor according to claim 23, wherein said microporous material has pores with an average diameter comprised between 0.10 mum and 0.50 mum.

25. The bioreactor according to claim 23, wherein said microporous material is constituted by polyether sulfone or the like.

26. The bioreactor according to claim 1, wherein the distribution density and the diameter of said fibers are constant throughout the extension of said first bundle and/or said second bundle.

27. The bioreactor according to claim 1, wherein the direction of the flow of said inoculated cells from said inoculation inlet through said structure has a component that is substantially perpendicular and a component that is substantially parallel to the longitudinal axis of said body.

28. The bioreactor according to claim 1, wherein the direction of the flow of said fluid from said inflow port to said outflow port through said structure is substantially parallel to the longitudinal axis of said body.

29. The bioreactor according to claim 1, wherein said fluid is plasma or ultrafiltrate.

* * * * *